United States Patent [19]
Kang et al.

[11] Patent Number: 5,978,440
[45] Date of Patent: Nov. 2, 1999

[54] TOMOGRAPHIC APPARATUS AND METHOD OF OBTAINING AN ARBITRARY CROSS-SECTIONAL IMAGE

[75] Inventors: Sung Taek Kang; Jae Hoon Jeong, both of Seoul, Rep. of Korea

[73] Assignee: Korea Academy of Industrial Technology, Seoul, Rep. of Korea

[21] Appl. No.: 08/977,946

[22] Filed: Nov. 25, 1997

[30] Foreign Application Priority Data

Nov. 28, 1996 [KR] Rep. of Korea ................. 96-59166

[51] Int. Cl.⁶ .................................................. G01N 23/00
[52] U.S. Cl. ................................................. 378/21; 378/22
[58] Field of Search ........................... 378/21–27, 98.8

[56] References Cited

U.S. PATENT DOCUMENTS

| | | |
|---|---|---|
| 4,688,241 | 8/1987 | Peugeot . |
| 5,081,656 | 1/1992 | Baker et al. . |
| 5,097,492 | 3/1992 | Baker et al. ................. 378/22 |
| 5,351,278 | 9/1994 | Koshishiba et al. .......... 378/22 |

OTHER PUBLICATIONS

Peters, Terence M., "Spatial Filtering to Improve Trnsverse Tomography", IEE Transactions on Biomedical Engineering, vol. BME–21, No. 3, May 1974, pp. 214–219.

*Primary Examiner*—David P. Porta
*Attorney, Agent, or Firm*—Ladas & Parry

[57] ABSTRACT

A tomographic apparatus for obtaining a cross-sectional image by fixing an X-ray source, and synchronously rotating an object under examination and a detector. According to the apparatus, the slope angle of the X-ray source can be sufficiently enlarged by the adjustment of the X-ray tube, and thus the precision of the obtained cross-sectional image can be heightened. Also, a method of obtaining a cross-sectional image of a three-dimensional object from an arbitrary direction and height.

5 Claims, 13 Drawing Sheets

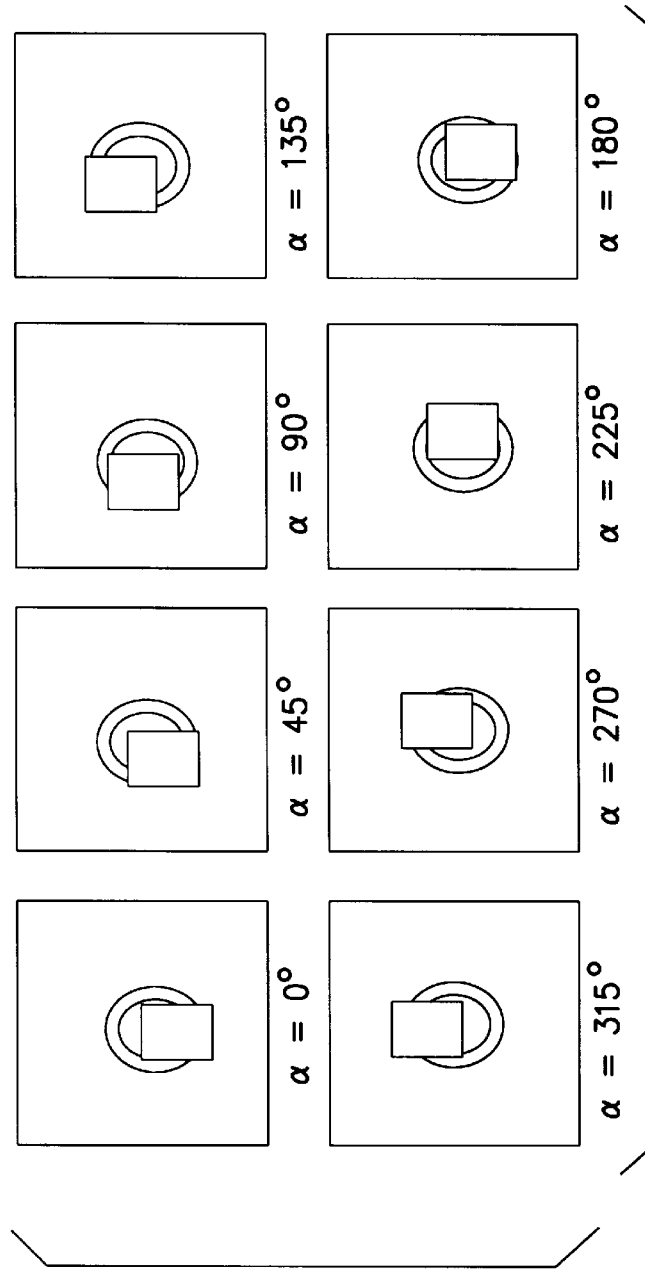
Fig. 9
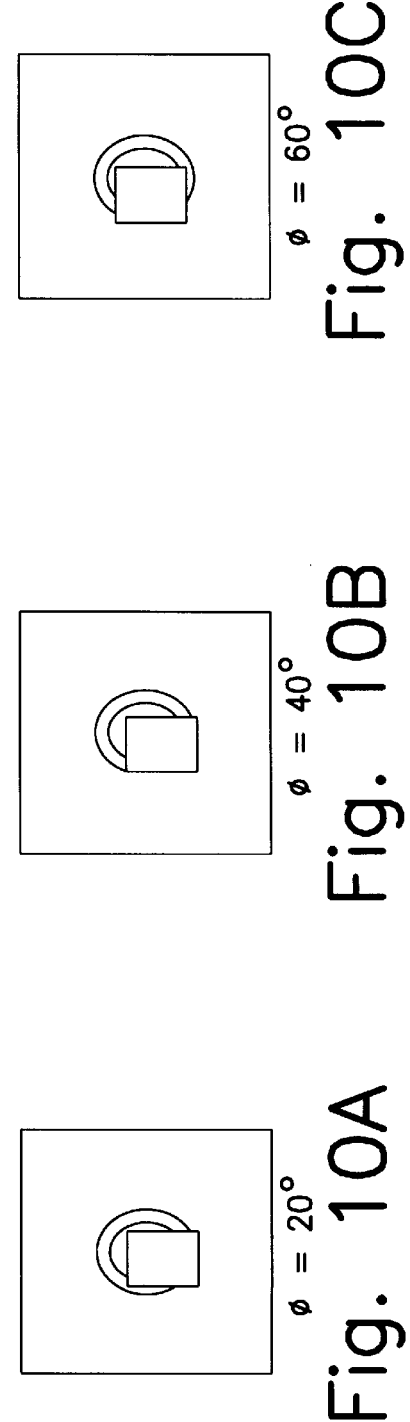
Fig. 10A
Fig. 10B
Fig. 10C

Fig. 11
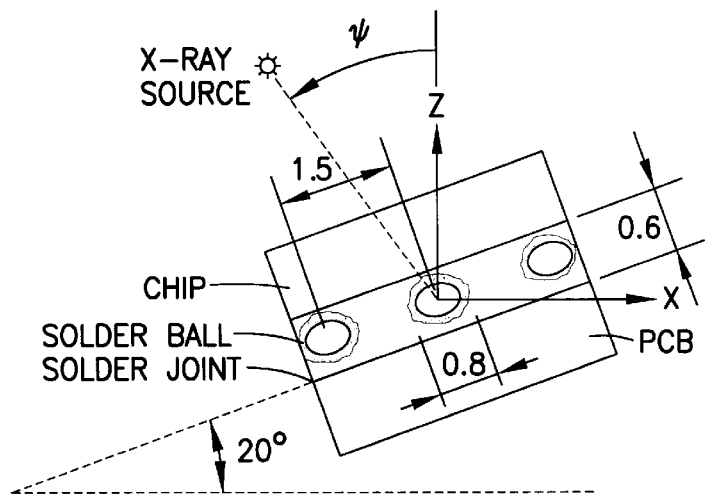
Fig. 13
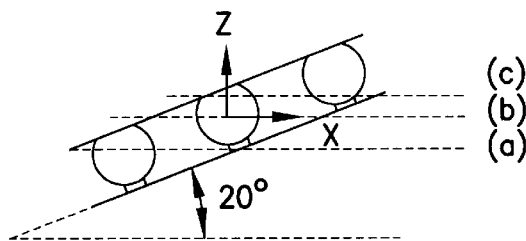
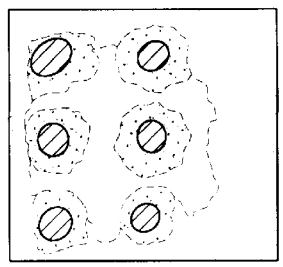
Z = − 0.4
(a)
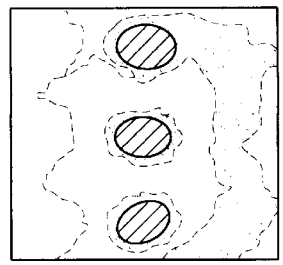
Z = 0
(b)
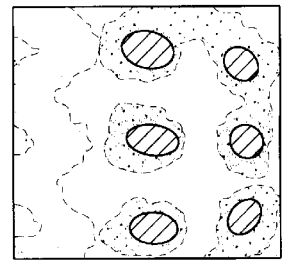
Z = 0.2
(c)

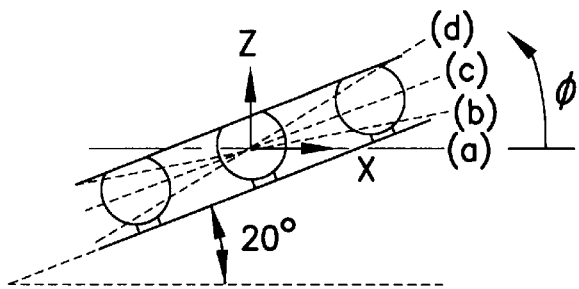
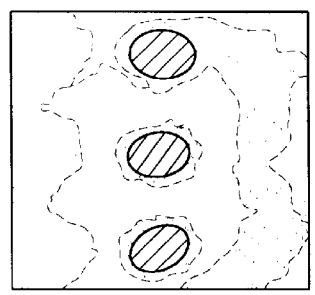
φ = 0°
(a)
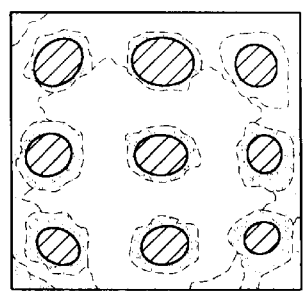
φ = 10°
(b)
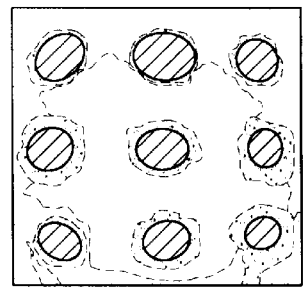
φ = 20°
(c)
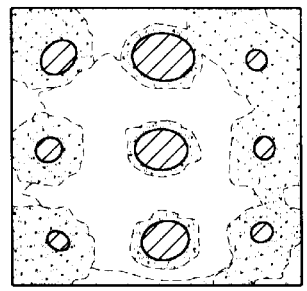
φ = 30°
(d)
Fig. 14

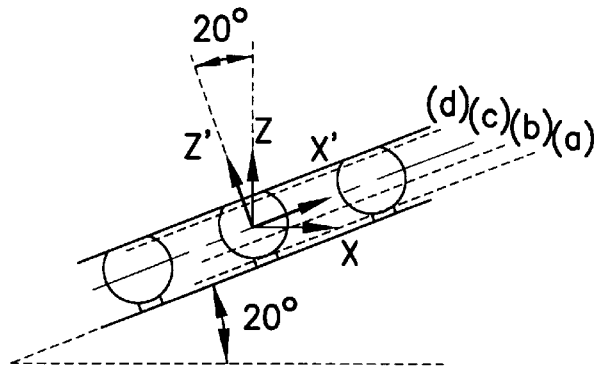
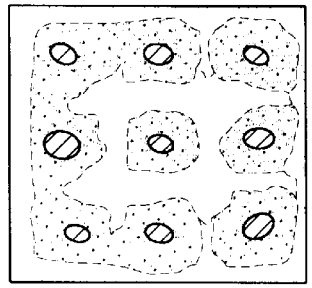
$Z' = -0.3$
(a)
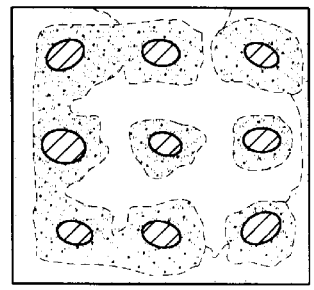
$Z' = -0.2$
(b)
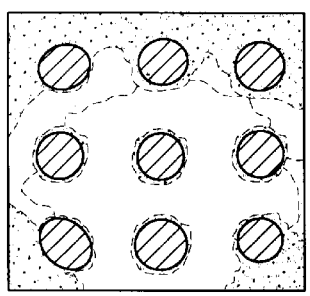
$Z' = 0$
(c)
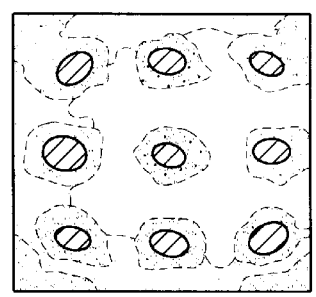
$Z' = 0.2$
(d)
Fig. 15

TOMOGRAPHIC APPARATUS AND METHOD OF OBTAINING AN ARBITRARY CROSS-SECTIONAL IMAGE

BACKGROUND OF THE INVENTION

1. Field of the Invention

The present invention relates to a tomography technique, particularly to a tomographic apparatus for obtaining a cross-sectional image by fixing an X-ray source and by synchronously rotating an object under examination with a detector. The present invention also relates to a method of obtaining a cross-sectional image of a three-dimensional object from an arbitrary angle and height by computational calculation utilizing the tomographic apparatus.

2. Description of the Prior Art

A tomographic apparatus is utilized in diverse fields. In the field of electronics, the tomography is particularly used for monitoring a soldering state on a substrate of an electronic circuit. The conventional methods of monitoring a soldering state by utilizing X-ray tomography can be roughly classified into two.

One method is a laminographic method for acquiring a cross-sectional image with a single image by synchronously rotating an X-ray source and a detector, and the other method is a digital tomosynthetic method for obtaining an average value of the images acquired during rotating an X-ray source in a computer.

U.S. Pat. No. 5,081,656 issued on Jan. 14, 1992 to Baker et al. discloses a laminography system utilizing a laminographic method. FIG. 1 briefly illustrates the example.

Referring to FIG. 1, an object under examination 1, a circuit substrate for instance, is laid in the middle of an X-ray source 2 and a detector 3. An image plane 6 of the object 1 is formed on a detector 3 by projecting an X-ray beam onto the object 1 from the X-ray source 2 synchronized around a common axis 4 and the detector 3. Particularly, the image plans 6 substantially lies in parallel with the planes 8, 9 defined by rotation of the X-ray source 2 and the detector 3.

Such a laminography utilizing the conventional laminographic method requires an X-ray tube which will rotate the X-ray source only to electronically rotate an X-ray beam. However, the X-ray tube is not only expensive but also generates a cross-sectional image of low precision due to the slope angle of the beam fixed to be under 30°. Also, the obtained cross-sectional image is unclear and is of low resolution.

U.S. Pat. No. 4,688,241 discloses a digital tomosynthetic method. Referring to FIG. 11 of U.S. Pat. No. 4,688,241, an X-ray source is projected (T1 to T8) while rotating in circle 480. This method is identical to the aforementioned method of projecting an X-ray in the laminography. A focus plane 484 of an object 456 is projected to the entering plans 494 of a large-scaled image amplifying tube 490. An image formed on a camera 494 is processed by a computer 500. This method has an advantage of processing the image in a digital value but requires an expensive scanning tube. Also, the cross-sectional image generated by this method is of low precision because the slope angle of the beam cannot be greater than 30°. The apparatus employing a large-scaled image amplifying tube (12") is expensive. Further, the image acquired by utilizing the periphery of the image intensifier of spherical shape is highly distorted.

SUMMARY OF THE INVENTION

An object of the present invention is therefore to provide a tomographic apparatus whereby a cross-sectional image of high precision to resolve the aforementioned problems can be obtained.

Another object of the present invention is to provide a method of obtaining a tomographic image of a three-dimensional object from arbitrary angles and heights by software based on images obtained by the tomographic apparatus.

To achieve the above objects, in one aspect of the present invention, there is provided a tomographic apparatus for obtaining a cross-sectional image, comprising: a fixed X-ray source; a rotating table on which an object is laid for being projected by an X-ray beam generated from the X-ray source; an image intensifier for converting the X-ray having passed through the object into a visible light; a detector for detecting the visible light having passed through the image intensifier to output an analog image signal; a frame grabber for storing and converting the analog image signal into a digital image signal; an image processing section for processing the digital image signal outputted from the frame grabber; a system control section for controlling the X-ray source and outputting a control signal according to the digital image signal processed by the image processing section; a motor control section for synchronously rotating the object and the detector according to the control signal from the system control section; and an output section for outputting the image signal processed by the image processing section.

To eliminate noise of the analog image signal generated during passing Slip-Ring, it is preferable that the detector is provided with a noise filter connected thereto. In the tomographic apparatus according to the present invention, the object and the detector synchronously rotate. Therefore, the slope angle of the X-ray source can be sufficiently increased by rotating the X-ray tube around the X-ray source, thereby heightening precision of the cross-sectional image.

In another aspect of the present invention, there is provided a method of obtaining a cross-sectional image, comprising the steps of: aligning a fixed X-ray source and a center of an image plans of an object with a center of a rotating detector; acquiring a plurality of images of the object with an arbitrary cycle by synchronously rotating the object and the detector; correcting distortions of the acquired images; and obtaining a cross-sectional image by synthesizing the corrected images.

Preferably, the step of obtaining the cross-sectional image may comprise the substeps of synthesizing the images of the object acquired from arbitrary directions, and synthesizing the images of the object acquired from an arbitrary height.

BRIEF DESCRIPTION OF THE DRAWINGS

The above objects, other features and advantages of the present intention will be more apparent by describing the preferred embodiment thereof with reference to the attached drawings, in which:

FIG. 9 represents a horizontal image set of the PCB substrate of FIG. 8 projected from an X-ray source from eight directions with a slope angle of 20°;

FIG. 10A is a synthesized result of the horizontal image set of FIG. 9;

FIG. 10B is a synthesized result of the horizontal image set realized with a slope angle of 40°;

FIG. 10C is a synthesized result of the horizontal image set realized with a slope angle of 60°;

FIG. 11 is a schematic diagram of a BGA package according to another preferred embodiment of the present invention.

FIG. 13 are tomograms synthesizing the tomograms of FIG. 12 with varied heights.

FIG. 14 are tomograms synthesizing the tomograms of FIG. 12 with an angle φ met to be 0 and projected with angle variations of φ to be from 0° to 30°; and FIG. 15 are tomograms synthesizing the tomograms of FIG. 12 acquired by projecting from varied heights against an axis Z' which is perpendicular to the slope plane.

DETAILED DESCRIPTION OF THE PREFERRED EMBODIMENTS

Figure 1:
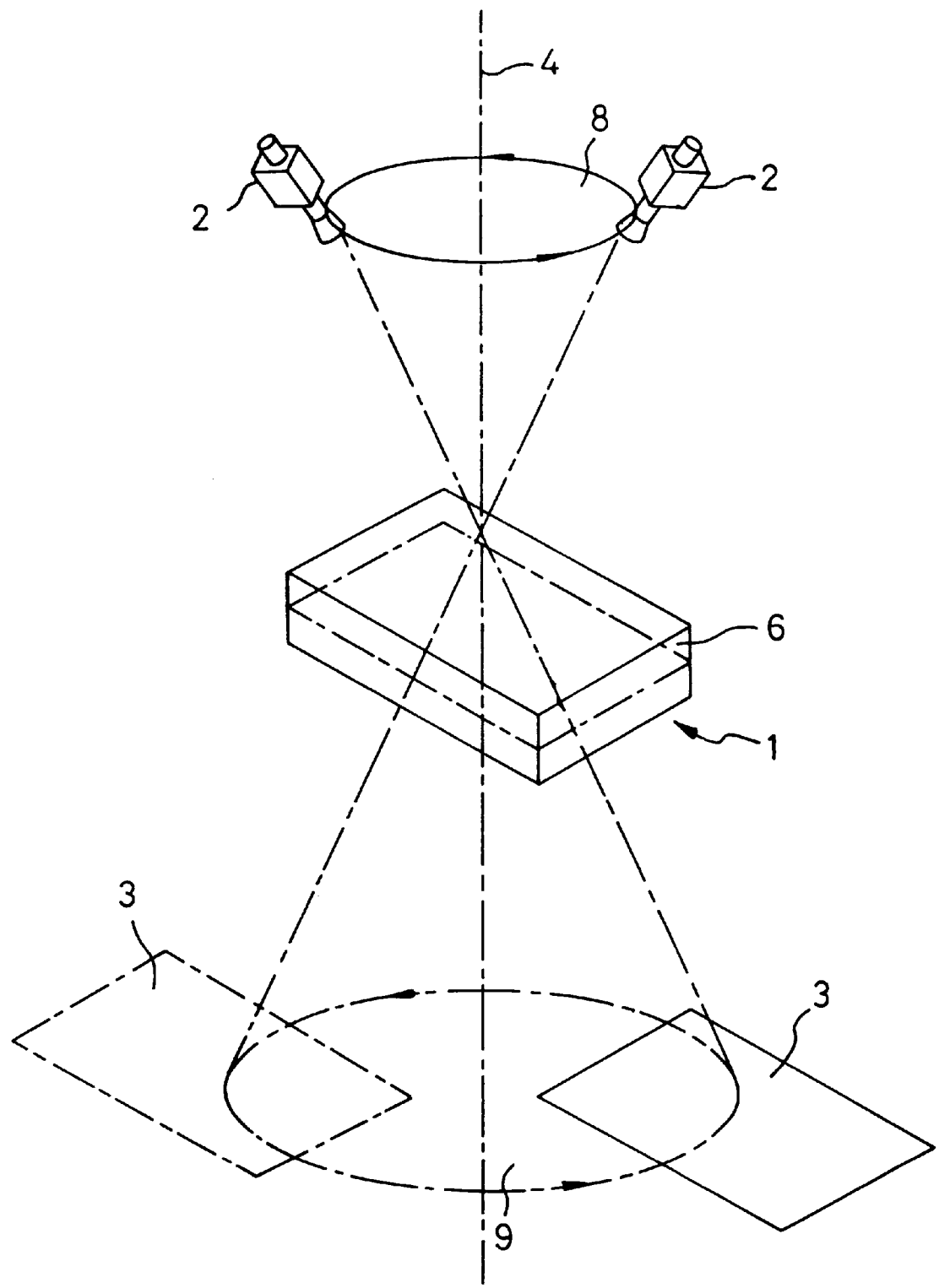
FIG. 1 is a view explaining principles of a conventional laminographic apparatus.
Figure 2:
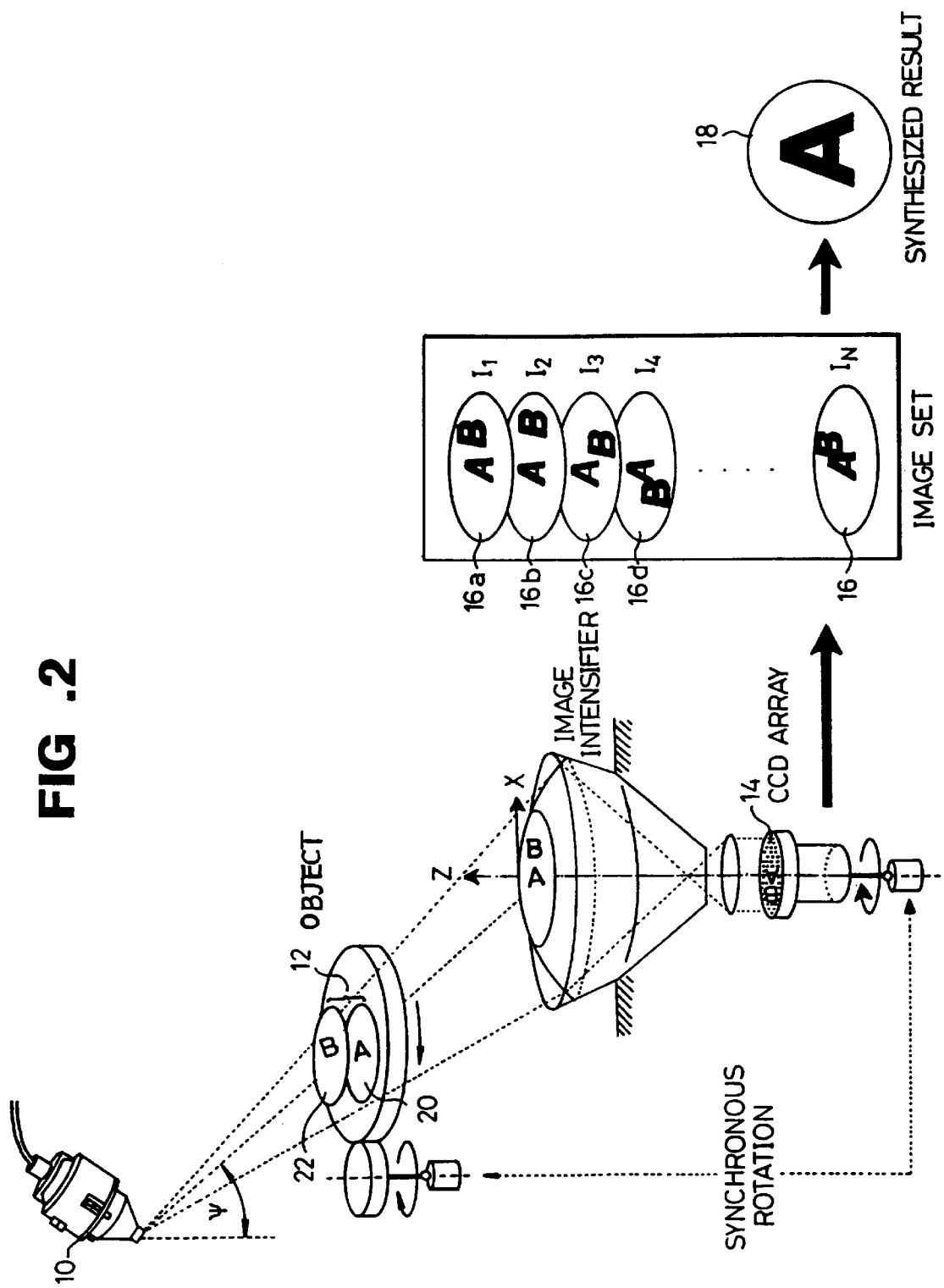
FIG. 2 is a view explaining principles of obtaining a cross-sectional image in a tomographic apparatus according to the present invention.

FIG. 2 is a view explaining the principles of obtaining a cross-sectional image by means of a tomography according to the present invention. Referring to FIG. 2, an X-ray source 10 is fixed, and an object 12 and a detector 14 synchronously rotate. While the object 12 and the detector 14 rotate once, an image is acquired every 1/N cycle. Thus, N images 16a, 16b, 16c, 16d are obtained eventually. A single cross-sectional image 18 can be obtained by synthesizing the N images $I_1, I_2, \ldots, I_N$.

Principles of obtaining a cross-sectional image from the N images will now be explained in detail. As described above, since the object 12 and the detector 14 synchronously rotate, a cross-section of a letter "A" on the focal plane 20 is always positioned at the same part of the detector 14. However, a cross-section of a letter "B" on the other plane 22 is positioned on a different part of the detector 14. Therefore, if the N cross-sectional images are synthesized, the cross-sectional image of the letter "B" on the other plane 22 becomes relatively blurred and eventually disappears in comparison with that of the letter "A". Thus, it becomes possible to realize a relatively sharp cross-sectional image 16 of the letter "A". The cross-sectional image becomes clearer if the number of images to be synthesized are increased. Particularly, as the slope angle ψ in the tomography of the present invention becomes greater, the separation between the focal plane 20 and the other plane 22 becomes greater, thereby heightening precision of the cross-sectional image.

Figure 3:
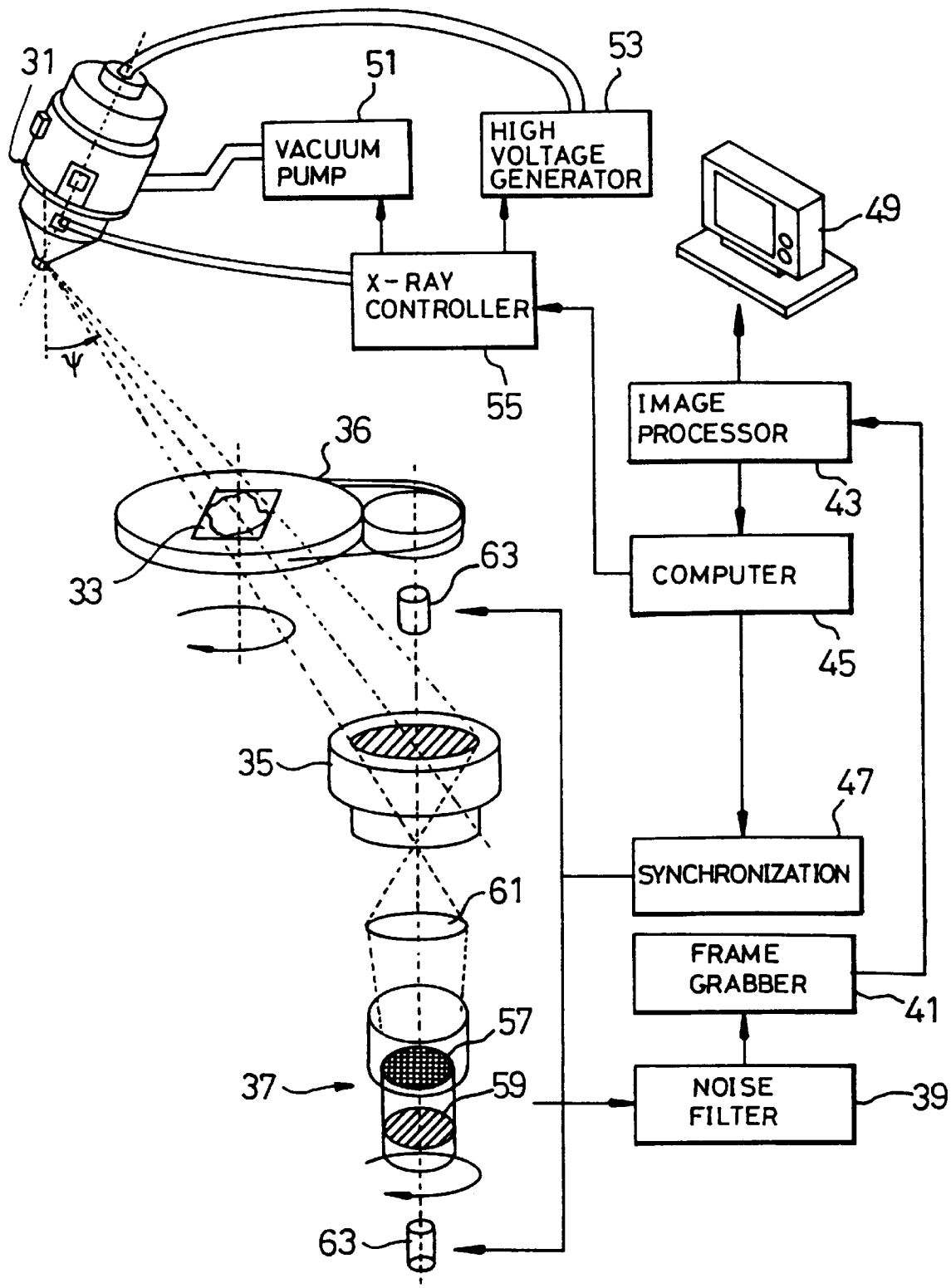
FIG. 3 In a view illustrating the structure of the tomographic apparatus according to the present invention.

FIG. 3 briefly illustrates a tomographic apparatus according to the present invention. The tomographic apparatus includes a fixed X-ray source 31 and a rotating table 36. An object 33 such as a printed circuit board is positioned on the rotating table 36. X-ray beam is projected to the object 33 from the X-ray source 313 After penetrating the object 33, the X-ray beam is converted to a visible light when penetrating an image intensifier 35. Then, the visible light is detected by the detector 37, which then converts the detected visible light to an analog image signal.

Noise is removed from the analog image signal outputted from the detector 37 by means of a noise filter 39, and the analog image signal is stored in a frame grabber 41. Then, the frame grabber 41 converts the analog image signal to a digital image signal. The digital image signal outputted from the frame grabber 41 is processed by the image processing section 43 to output the resulting image signal. The system control section 45 receives a command from the image processing section 43 and generates a control signal based on the input digital image signal to control the X-ray source. As a motor control section 47 synchronously rotates two submotors 63 in response to a control signal generated from the system control section 45, the object 33 connected to the servomotors 63 and the detector 37 synchronously rotate.

In a tomography of the present invention, a vacuum pump 51, a high voltage generator 53 and an X-ray controller 55 are connected to the X-ray source. The detector 37 comprises a charge coupled device (CCD) 57 and a Slip-Ring 59. The Slip-Ring 59 is for transmitting a signal only without twisting a signal cable or a control cable while rotating the detector 37. It is possible to magnify a corrected image by providing a lens 61 between the image intensifier 35 and the detector 37. It is also possible to process an image faster by using a digital signal processor (DSP) in the image processing section 43.

Figure 4:
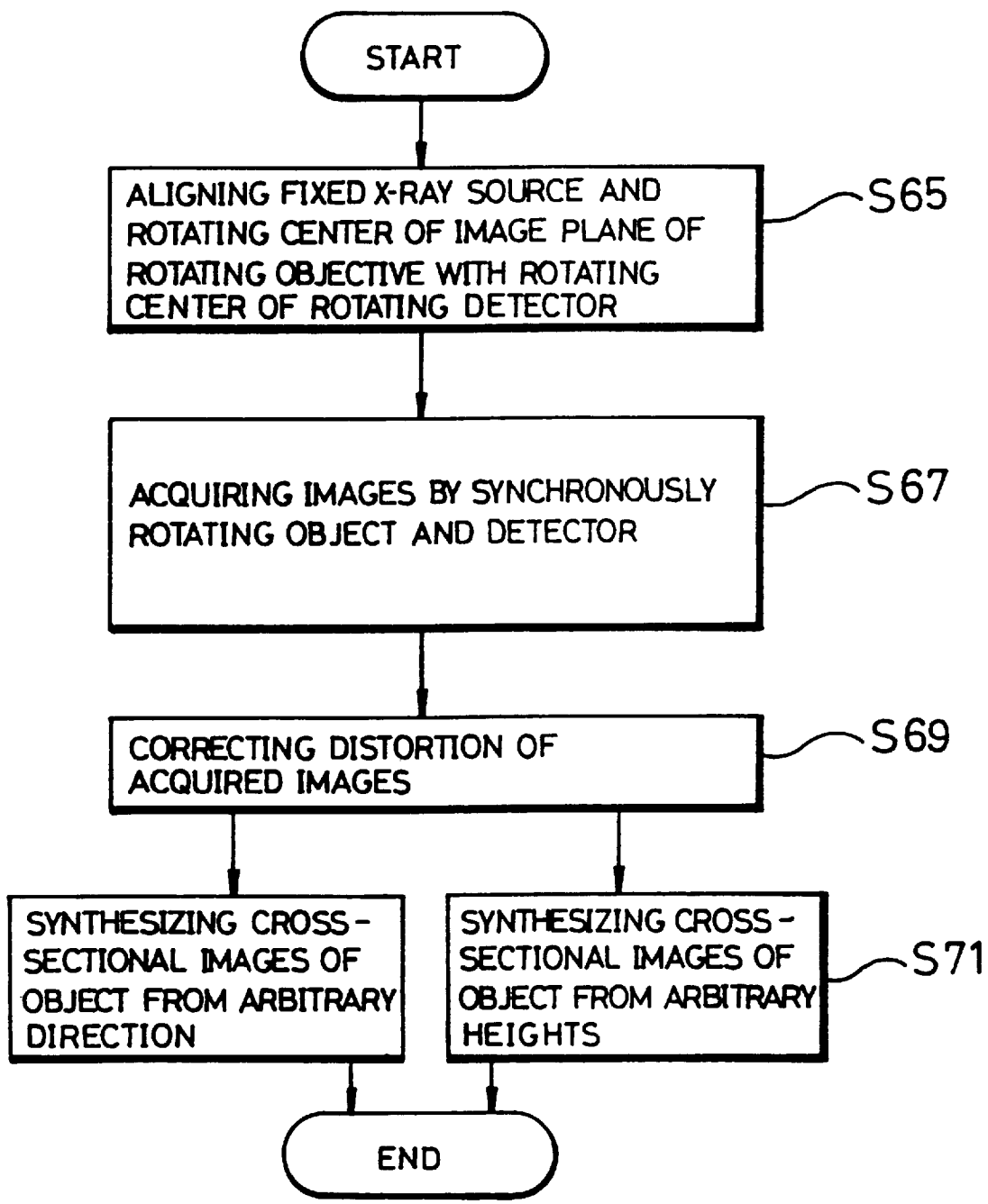
FIG. 4 is a flowchart incorporating the method of obtaining a cross-sectional image according to the present invention.

The method of realizing a cross-sectional image according to the present invention will now be explained with reference to FIGS. 3 and 4.

The X-ray source 31 is synchronized with the rotating centers of the cross-sectional plane of the object 33 and the detector 37. Next, the object 33 and the detector 37 are synchronously rotated while maintaining the respective rotating centers. Images are realized with arbitrary cycles while the object 33 and the detector 37 rotate once (S67). Such images are acquired through the image intensifier 35, the incident surface of which is curved. Thus, the acquired images are distorted, and this image distortion should be corrected before synthesizing (S69). It is possible to either synthesize the distortion-corrected images into a single horizontal cross-sectional image (S71) or realize cross-sectional images from arbitrary angles or heights.

In general, a cross-sectional image of a three-dimensional object can be realized by synthesizing multiple images acquired while the X-ray source rotates once. The cross-sectional image realized in this manner is a horizontal cross-sectional image of the focal plane of the object. The focal plane means a horizontal plane including the rotating center. If it is possible to realize varied cross-sectional images of a three-dimensional object from arbitrary angles and heights by means of a computer software based on the images acquired by means of the tomography, re-correction will be unnecessary, and shorter time will be consumed for realizing the cross-sections of different anlges and heights.

I. ARBITRARY ANGLE PROJECTION

Figure 5:
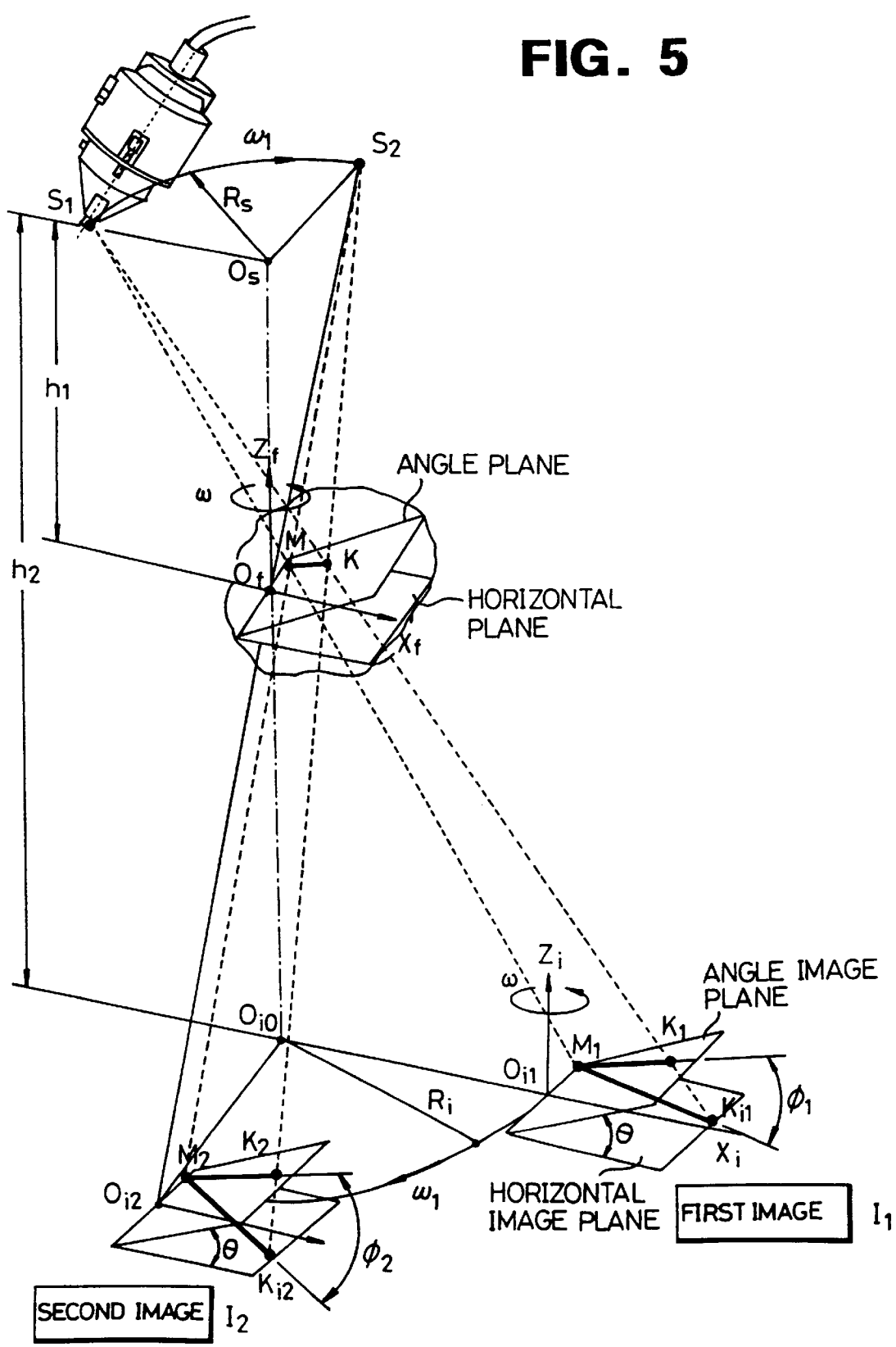
FIGS. 5 to 7 are diagrams briefly explaining the procedure of the tomographic method according to the present invention.

According to one feature of the present invention, it is possible to reconstruct a cross-sectional image on a plane of a three-dimensional object for arbitrary angles. FIG. 5 in a schematic diagram briefly illustrating the drawings for reconstructing a cross-sectional image on a plane for an arbitrary anlge (a slope plane).

Referring to FIG. 5, the X-ray source $S_1$ is fixed, while an object and an image plane synchronously rotate around the rotating centers $O_f$, $O_{i1}$. Supposing an arbitrary straight line MK on arbitrary angle (θ) plane of the object, the straight line MK in projected as $M_1K_{i1}$ on the horizontal image planes. After a synchronous rotation of the object with the image plane, $M_1K_{i1}$ is projected as $M_2K_{i2}$ on the horizontal image planes. A second image is illustrated as a projection result for $S_2$ position wherein the X-ray source is rotated by $\omega_1$ for convenience' sake. This phenomenon is according to the Laminography principle. A cross-sectional image can be realized for an image for a direction angle θ with the horizontal plane by projecting the straight line $M_2K_{i2}$ from the horizontal images onto the angle (θ) slope image planes and by synthesizing the slope images, because the straight line $M_1K_1$ is imaged on the name position with the same size as the straight line $M_2K_{i2}$. Therefore, the following equations are obtained.

$$\frac{MK}{M_1K_1} = \frac{MK}{M_2K_2} = \frac{H_o}{H_1} \tag{1}$$

$$M_1K_1 = M_2K_2 = \frac{H_1}{H_o}MK \tag{2}$$

Equation (2) represents that the straight lines with the same slope angle projected to each angle image plane has the same length. Therefore, it is possible to realize the cross-sectional image of an arbitrary angle plane of the object by synthesizing the images projected to each angle image plane. The cross-sectional image can be obtained according to the Laminography principle. Since the slope angles ($\phi_1$, $\phi_2$, . . . , $\phi_k$) are changed according to the synchronous rotation of the X-ray source, not only the length of the straight line $M_kK_k$ but also the slope angles $\phi_k$ of the line $M_kK_k$ should be calculated for the exact synthesis of an image set. For the derivation of mathematical formulas, a schematic diagram is represented in FIG. 6.

Figure 6:
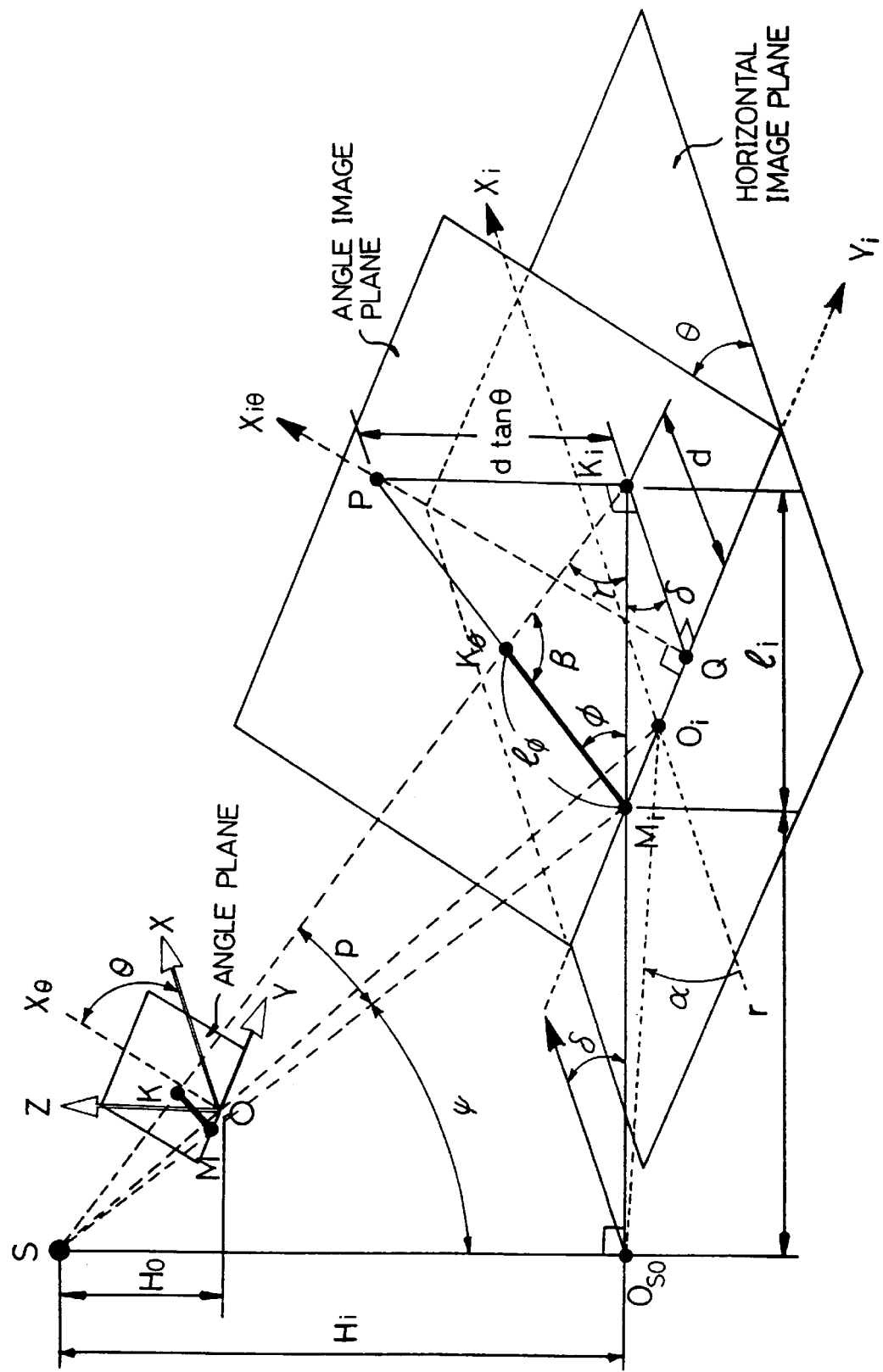

Calculation or slope angle φ:

In FIG. 6, two image planes are represented; one is the horizontal plane including an arbitrary point $K_1$, and the other is the upper part of the angle image plans with a slope angled θ to this horizontal plane. A point P on the angle image plane is defined as an intersection with a line starting from a point $K_1$ and normal to the-horizontal plane. Also, a point $M_1$ is defined as the intersection of the $Y_i$ axis with the line $O_{so}K_i$. The distance between the point $K_i$ and the point P is dtan θ. And the distance $l_i$ between the point $M_i$ and the point $K_i$ is calculated as d/cos δ. Here, d is the distance to the $Y_i$ axis from the point $K_i$, and δ is the gap angle between the line $O_{so}K_i$ and $X_i$ axis. Therefore, the slope angle φ is calculated as $$\phi = \tan^{-1}\left(\frac{d\tan\theta}{l_i}\right) \tag{3}$$

In the lower part of the angle image plane, the formula for the slope angle φ is the same as the expression (3).

Calculation of length $l_\phi$:

The length $l_\phi$ is the distance of the point $M_1$ to the point $K_\phi$ which is a point projected from the point $K_i$ to the angle image plane, and $l_\phi$ is a generalized variable to express the position of the point $K_\phi$ in the angle image plane according to the rotation of the X-ray source. If the sine law is applied to $\Delta M_iK_iK_\phi$, $$\frac{l_i}{\sin\beta} = \frac{l_\phi}{\sin\gamma} \tag{4}$$

Here, β and γ are the inside angles of $\Delta M_iK_iK_\phi$, and are calculated as follows.

$$\beta = 90 - (\phi - \phi - \rho) \tag{5}$$

$$\gamma = 90 - (\phi + \rho) \tag{6}$$

Here, the expression (4) becomes $$l_\phi = l_i \sin\frac{\gamma}{\sin\beta} = \tag{7}$$

$$l_i \cos\frac{(\varphi + \rho)}{\cos(\phi - (\psi + \rho))} = l_i \cdot \frac{\sin[90 - (\varphi + \rho)]}{\sin[90 - (\varphi - (\psi + \alpha))]}$$

Here, applying the relation of cos(A±B)=cos Acos B±sin Asin B to the expression (7), $$l_\varphi = l_i \cdot \frac{1}{\cos\varphi + \sin\varphi \cdot \tan(\varphi + \rho)} \tag{8}$$

while $$\tan(\varphi + \rho) = \frac{\gamma + l_i}{H_i} \tag{9}$$

and γ can be calculated as follows.

$$\gamma = \frac{H_i \tan\varphi_0 \cos\alpha}{\cos\delta} \tag{10}$$

Here, $\psi_o$ is the angle between the Z axis and the line from the X-ray source S to the center point $O_i$ of the image plane. The following expression can be obtained from equations (8) and (9).

$$l_\varphi = \frac{l_i}{\cos\varphi + \sin\varphi \cdot \frac{\gamma + l_i}{H_i}} \tag{11}$$

Since the signs of the expression (11) are changed according to the rotation angle a of the X-ray source and arbitrary angle θ of the object, the generalized expression can be written using sign-parameters as follows, $$l_\varphi = \frac{l_i}{a_{11}\cos\phi + a_{22}\sin\phi \frac{a_{33}\gamma + a_{44}l_i}{H_i}} \tag{12}$$

where, $a_{11}$, $a_{22}$, $a_{33}$, $a_{44}$ are given in Table 1 below.

The slope cross-sectional image from an arbitrary direction can be realized by reconstructing and synthesizing the slope image of the slope angle φ and slope length 1φ for each image from the expressions (3) and (12), respectively.

TABLE 1

| Rotation angle of X-ray source (α) | Slope angle of the object plane (φ) | | | | | | | |
|---|---|---|---|---|---|---|---|---|
| | 0° < α < 180° | | | | 180° < α < 360° | | | |
| | $a_{11}$ | $a_{22}$ | $a_{33}$ | $a_{44}$ | $a_{11}$ | $a_{22}$ | $a_{33}$ | $a_{44}$ |
| 0° < α < 180°, 180° < α < 270° | 1 | 1 | 1 | 1 | 1 | 1 | 1 | 1 |
| α = 90°, α = 270° | 1 | 1 | 0 | 1 | 1 | −1 | 0 | 1 |
| 90° < α < 180°, 270° < α < 360° | 1 | −1 | 1 | −1 | 1 | 1 | 1 | −1 |

II. ARBITRARY HEIGHT PROJECTION

Figure 7:
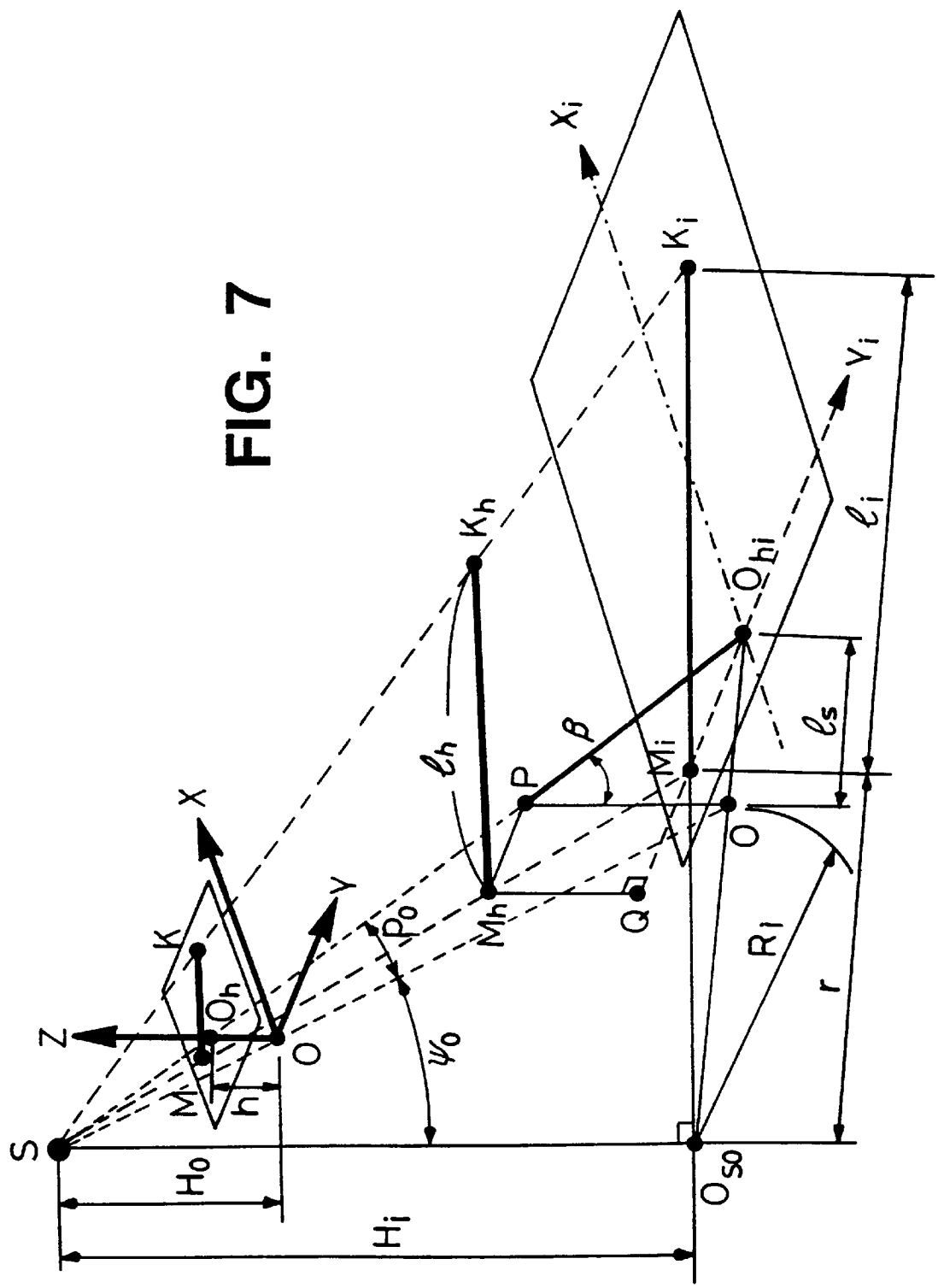

FIG. 7 represents a schematic diagram for arbitrary height projection. Supposing reconstruction of the cross-sectional image for the horizontal plane spaced part from the focal plane of the object by h, the straight line MK on the height plane is magnified and projected to $M_i K_i$ on the image plans and the image center point $O_{hi}$ for the height plane is shifted by $l_s$ from the center point $O_i$ for the focal plane in the image plane. Hence, it is possible to realize the cross-sectional image for arbitrary height plane of the object by calculating the shifted distance $l_s$ and the real size $l_h$ of the projected line $M_i K_i$.

(1) Cross-sectional image for arbitrary height plane above the focal plane

Derivation of the shift distance $l_s$:
From Δ $O_i$ $O_{hi}$P, $$l_s = h' \tan \beta \quad (13)$$

Since Δ $SOO_h$ and Δ $SO_i P$ are similar figures, $$h' = \frac{H_i}{H_o} h \quad (14)$$

Also, the relation, $\beta = \psi_o + \rho_o$, gives $$\tan \beta = \tan(\psi_o + \rho_o) = \frac{R_i + l_s}{H_i} \quad (15)$$

Therefore, from the expressions (14) and (15), $l_s$ is expressed as $$l_s = \frac{R_i h}{H_o - h} \quad (16)$$

Derivation of the real size $l_n$: Since $\Delta SM_h K_h$ and $\Delta SM_i K_i$ are similar figures, it is possible to derive the formulas in the same manner as follows.

$$l_h = \left(1 - \frac{h}{H_o}\right) l_i \quad (17)$$

(2) Cross-sectional image for arbitrary height plane below the focal plane

In the case that the height plane to be obtained is below the focal plane, the formulas can be derived in the same manner as follows.

$$l_s = \frac{R_i h}{H_o + h} \quad (18)$$

$$l_h = \left(1 + \frac{h}{H_o}\right) l_i \quad (19)$$

Therefore, a cross-sectional image for arbitrary height projection can be realized by reconstructing the images for arbitrary heights from the expressions (16) to (19).

Figure 8:
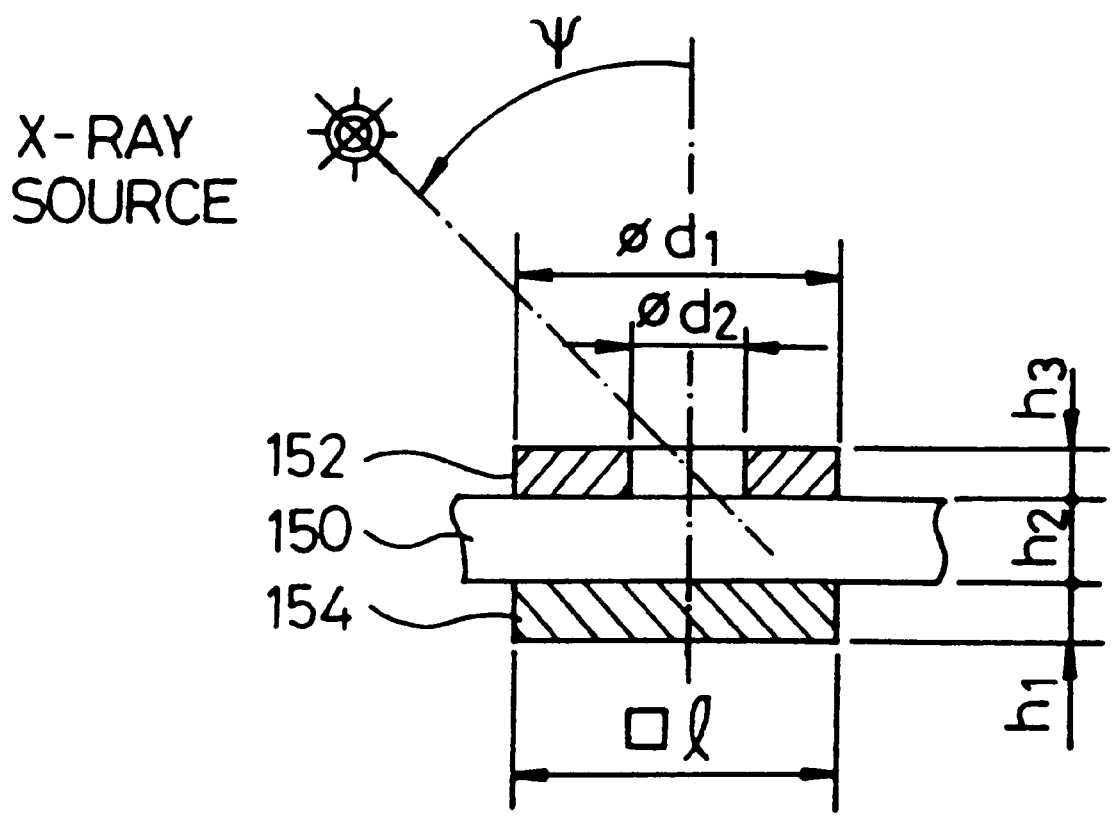
FIG. 8 is a schematic diagram illustrating a PCB substrate according to a preferred embodiment of the present invention, on the upper face of which a ring-shape fitting is mounted, and on the lower face of which a rectangular fitting is mounted.

Embodiment 1:

FIGS. 8 to 10 illustrate the first embodiment of the cross-sectional image obtained by the tomography according to the present invention.

Referring to FIG. 8, the object used in a PCB substrate 150 to which a ring-type fitting 152 and a rectangular-type fitting 154 are vertically attached. The PCB substrate 150 had a thickness of 1.6 mm. The ring-type fitting 152 had a thickness of 0.2 mm with the size of 0.2 mm×4×4 mm.

FIG. 9 represents X-ray tomograms projected from eight directions with the slop angle φ to the X-ray source 31 being 20° against the PCB substrate. FIG. 10A represents a synthesis of each tomogram in FIG. 9. FIG. 10B represents a synthesis of the tomograms projected with the slope angle of 40°, while FIG. 10C represents a synthesis of the tomograms projected with the slope angle of 60°.

Referring to FIG. 10A, afterimages remain in the middle of the ring where the rectangular-type fitting rotates and overlaps. On the other hand, such afterimages tend to disappear according to increase of the slope angle from 40° to 60°. As shown in FIG. 10C, the afterimages completely disappear when the slope angle increased to 60°. As a result it can be recognized that according to the present invention, a higher-precision cross-sectional image can be obtained in comparison to the conventional apparatus utilizing the slope angle below 30°.

Embodiment 2:

Referring to FIGS. 11 to 15, the tomography for obtaining the cross-sectional image according to a second embodiment of the present invention will be explained.

FIG. 11 represents the photograph of the BGA package used for experiments. Since the soldering state of the solder joints in a BGA package has a serious effect upon the product, the monitoring of the solder joints using an X-ray source is important. However, the soldering state is not analyzed properly by the transmissive image because of the influence of the solder ball with its high-content lead. Therefore, the cross-sectional image of the solder parts should be obtained to accurately recognize the state of the solder joints. According to the present invention, to show the realized results of the cross-sectional image for arbitrary height and arbitrary angle plane, the BGA package with a slope angle to the horizontal plane was taken as an object for experiments. The BGA package used for experiments has a tilt angle 20° to the horizontal plane. The diameter of the BGA balls is 0.8 mm, the gap distance from chip to PCB is 0.6 mm and the pitch between balls is 1.5 mm. We acquired the image set for the center plane of the solder ball and reconstructed the cross-sectional images for arbitrary height and arbitrary angle planes using this image set. To clearly verify the result of the cross-sectional image, the BGA package with insufficient solder volume was used in experiments.

Figure 12:
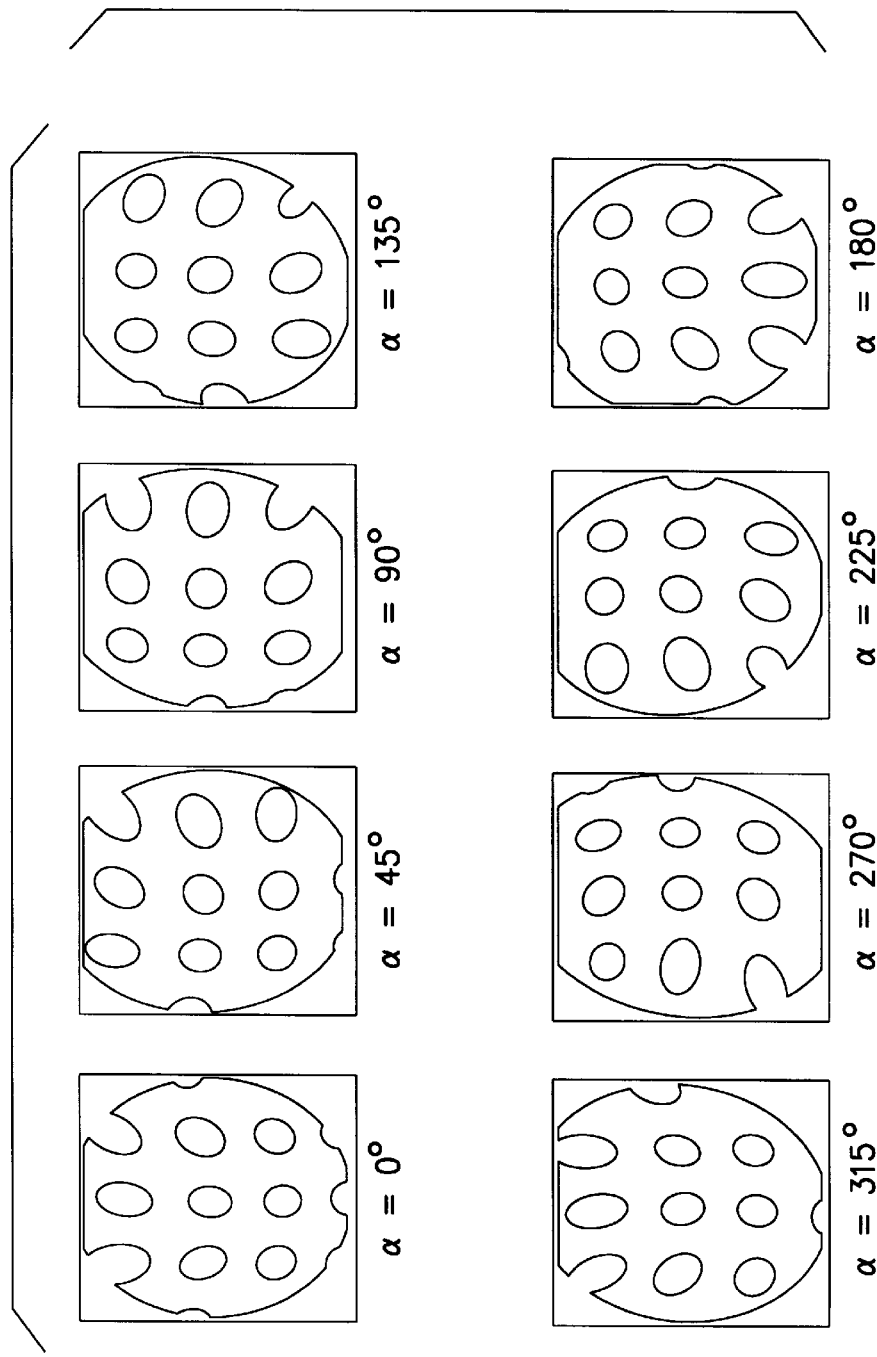
FIG. 12 are tomograms illustrating an image set acquired from eight directions.

FIG. 12 represents the image set acquired from 8 directions. Focal plane is located at the center of the solder ball, the viewing angle(ψ) of the X-ray source is 30 degrees, Ho(X-ray source-object distance) is 15.5 mm and Hi(X-ray source-detector distance) is 330 mm. For the exact synthesis, pin-cushion errors due to the transmission directions of the X-ray source were compensated. The synthesis was achieved by averaging the 8-images. The result of the synthesis is represented in FIG. 13(b). This figure shows the cross-sectional image only for the balls on the focal plans. The balls of out-of-the focal plane were blurred. Next, the height projection for Z=−0.3 mm was performed to obtain the image for the solder joints. For this projection, the image set (FIG. 12) acquired for the focal plane was used. The synthesis result was represented in FIG. 13(a). The solder joints of the center row blurred in FIG. 13(b) are shown in this image. However, since it is image of the plane for a tilt of an angle 20°, it is difficult to obtain the exact information for the soldering state from this image. This time, the horizontal cross-sectional image for Z=+0.2 mm was realized. The height projection from the same image set achieved and then synthesized. The resulting image is represented in FIG. 13(c). It is shown that the cross-sectional images for the desired plane of the balls were remained and the ones of the other balls were blurred. We could obtain only the partial information for the solder joints of the BGA package with a tilt angle from the horizontal cross-sectional images in FIGS. 13(a) to 13(c). Therefore, the angle projection for arbitrary slope angle plane is required to realize the cross-sectional image for the solder joints of all balls of a BGA package simultaneously and exactly.

Accordingly, the cross-sectional image for the slope angle should be obtained. The cross-sectional image for the slope angle was realized by calculation according to expression 12 derived hereinbefore utilizing the images of FIG. 12.

The angle $\delta$ was set to 0 degree, the angle $\phi$ was varied from 0 degree to 30 degrees. The result of the slope angle cross-sectional realization is represented in FIG. 14. The diameters of the balls of the right and left row became larger according to the increase of the angle $\phi$, differently from the result for $\phi=0°$. When the slope angle is 20 degrees, it represents that all balls appear most perfectly with same diameter in FIG. 14, since the angle projection was carried out for the same angle as the tilted plane. It means that the balls of the BGA package are parallel to the PCB plane. Therefore, it can be said that the angle projection should be performed by the same angle as the tilted plane to realize most exactly the cross-sectional image for an object with a tilt angle. When the slope angle was set to 30 degrees, the ball size of the right and left row became smaller again as FIG. 14(d). The above experimental results show that the realization of the cross-sectional images by the angle projection was achieved well.

Next, the angle projection was performed for the same degrees as the tilt angle (20°), and then the height projection were performed according to the axis perpendicular to the tilted plane. First, the angle projection was achieved for $\phi=20°$ and Z=0, and then using the images acquired here, the height projections for several heights were accomplished according to the Z' axis perpendicular to the tilted plane. The realized result of the cross-sectional images was represented as FIG. 15. The FIG. 15 shows that the diameters or the cross-sectional images of the desired planes are varied clearly in accordance with the height of the Z' axis. The cross-sectional image at Z'=−0.3 mm is the important one, because the image is for the solder joints to be inspected. The size of the diameters in the image can be used as the information to estimate the soldering state (excess solder, insufficient solder, no solder, etc.). The blurred image appeared around the ball images at the heights of Z'≠0 as shown in FIG. 18. The reason is that the image for the other plane bigger than the desired plane is blurred at the surroundings of the image for the desired plane when the images are synthesized. However, if the synthesized image with a blurred portion in digitized by a suitable threshold value, the blurred portion will be vanished and then, only the diameter of the cross-sectional image to be inspected can be obtained obviously. From the above experiments, if can be said that the cross-sectional images for a BGA package with an arbitrary slope angle to the horizontal plane wall realized by the angle projection and the height projection.

As described above, according to the present invention the slope angle of the X-ray source can be sufficiently enlarged by the adjustment of the X-ray tube, and thus the precision of the obtained cross-sectional image can be heightened. As a result, the present invention can be applied to the cross-sectional inspection of high-precision components.

While the present invention has been described and illustrated herein with reference to the preferred embodiment thereof, it will be understood by those skilled in the art that various changes in for and details may be made therein without departing from the spirit and scope of the invention.

What is claimed is:

1. A tomographic apparatus for obtaining a cross-sectional image, comprising:

a fixed X-ray source;

a rotating table on which an object is laid for projecting an X-ray beam generated from said fixed X-ray source directly onto said object;

said rotating table being adjustable in angle with respect to the horizontal between 0° and 60°;

an image amplifying tube for converting the X-ray beam passing through the object into a visible light image;

a detector for detecting the visible light image to output an analog image signal;

a frame grabber for storing and converting the analog image signal into a digital image signal;

an image processing section for processing the digital image signal outputted from the frame grabber taking into account the angle between the table and the horizontal;

a system control section for controlling the fixed X-ray source and outputting a control signal according to the digital image signal processed by the image processing section;

a motor control section for synchronously rotating the object and the detector according to the control signal from the system control section; and an output section for outputting the image signal processed by the image processing section.

2. The apparatus as claimed in claim 1, wherein said detector includes a noise filter, connected thereto, for removing noise of said analog image signal.

3. The apparatus as claimed in claim 1, wherein said detector comprises a charge coupled device and a Slip-Ring.

4. A method of obtaining a cross-sectional image, comprising the steps of:

aligning a fixed X-ray source and a rotating center of a table defining an image plane of an object on said table with a center of a rotating detector;

projecting a beam from said X-ray source directly onto said object;

providing adjustment of said table with respect to the horizontal to enable said table to assume an angle of up to 60° with respect to the horizontal;

acquiring a plurality of images of the object by synchronously rotating the object and the detector;

correcting distortions of the acquired images; and obtaining a cross-sectional image by synthesizing the corrected images.

5. The method as claimed in claim 4, wherein said step of obtaining the cross-sectional image comprises the substeps of:

synthesizing the images of the object acquired from arbitrary directions and synthesizing the images of the object acquired from arbitrary heights.

* * * * *

UNITED STATES PATENT AND TRADEMARK OFFICE
CERTIFICATE OF CORRECTION

PATENT NO.   : 5,978,440
DATED        : November 2, 1999
INVENTOR(S)  : Sung Taek Kang It is certified that error appears in the above-identified patent and that said Letters Patent is hereby corrected as shown below:

<u>Title page,</u>
Item [73], "Korea Academy of Industrial Technology: should read -- Korea Electronics Technology Institute -- and "Seoul" should read -- Masan -- Ri --.

Signed and Sealed this

Fifth Day of February, 2002

Attest:

JAMES E. ROGAN
*Attesting Officer*   *Director of the United States Patent and Trademark Office*